US008789410B2

(12) United States Patent
Dardelin et al.

(10) Patent No.: US 8,789,410 B2
(45) Date of Patent: Jul. 29, 2014

(54) DEVICE FOR MONITORING METAL WIRES IN A TIRE

(75) Inventors: Thierry Dardelin, Coumon d'auvergne (FR); Patrice Alcalde, Simpsonville, SC (US); Jean-Marc Decitre, Marcoussis (FR); Olivier Casula, Longport-sur-orge (FR)

(73) Assignees: Michelin Recherche et Technique S.A., Granges-Paccot (CH); Compagnie Generale des Etablissments Michelin, Clermont-Ferrand (FR)

( * ) Notice: Subject to any disclaimer, the term of this patent is extended or adjusted under 35 U.S.C. 154(b) by 424 days.

(21) Appl. No.: 13/142,386

(22) PCT Filed: Dec. 28, 2009

(86) PCT No.: PCT/FR2009/052709
§ 371 (c)(1),
(2), (4) Date: Jan. 25, 2012

(87) PCT Pub. No.: WO2010/076532
PCT Pub. Date: Jul. 8, 2010

(65) Prior Publication Data
US 2012/0137761 A1 Jun. 7, 2012

(30) Foreign Application Priority Data
Dec. 31, 2008 (FR) ...................... 08 59166

(51) Int. Cl.
*E01C 23/00* (2006.01)
*G01M 17/02* (2006.01)
*G01N 27/90* (2006.01)
*G01N 33/00* (2006.01)

(52) U.S. Cl.
CPC ........... *G01M 17/02* (2013.01); *G01N 27/9013* (2013.01); *G01N 2033/0085* (2013.01)
USPC ............... 73/146; 324/232; 324/238

(58) Field of Classification Search
CPC .............. G01M 17/02; G01N 27/9013; G01N 2033/0085
USPC .............................. 73/146; 324/240
See application file for complete search history.

(56) References Cited

U.S. PATENT DOCUMENTS

| 4,004,693 A | 1/1977 | Tsuji et al. |
| 4,427,940 A * | 1/1984 | Hirama et al. ................. 324/240 |

(Continued)

FOREIGN PATENT DOCUMENTS

| CN | 1169776 | 1/1998 |
| EP | 27368 A2 * | 4/1981 ............. G01N 27/72 |

(Continued)

OTHER PUBLICATIONS

Office Action dated Jun. 6, 2013 from the Chinese Patent Office for corresponding Application No. 2009-80153115.1.

(Continued)

*Primary Examiner* — Lisa Caputo
*Assistant Examiner* — Roger Hernandez-Prewit
(74) *Attorney, Agent, or Firm* — Cozen O'Connor (57) ABSTRACT

The device (18) for checking a tire (14) reinforcing thread comprises: an induction member (68, 70) that induces a magnetic flux (P1, P2; P) in the thread (42a-b; 100; 102), a support (67) supporting the induction member (68, 70) having the overall shape of a U and comprising legs (82, 84) that conduct the magnetic flux (P) into the thread (42a-b; 100; 102), the legs defining a direction of alignment of the device, at least one receiver member (74) that receives the magnetic flux (P1, P2; P) flowing through the thread (42a-b; 100; 102) situated between the legs (82, 84). The dimensions of the receiver member are designed so as to measure only the magnetic flux flowing through the thread (42a-b; 100; 102) when, in operation, the direction of alignment (18) is parallel to the thread (42a-b; 100; 102).

17 Claims, 5 Drawing Sheets

(56) References Cited

U.S. PATENT DOCUMENTS

| | | | |
|---|---|---|---|
| 5,570,017 A * | 10/1996 | Blum | 324/232 |
| 5,717,332 A * | 2/1998 | Hedengren et al. | 324/229 |
| 6,005,388 A | 12/1999 | Kaefer-Hoffmann et al. | |
| 6,016,695 A * | 1/2000 | Reynolds et al. | 73/146 |
| 6,057,684 A | 5/2000 | Murakami et al. | |
| 8,436,607 B2 * | 5/2013 | Alport et al. | 324/232 |
| 2006/0217110 A1 | 9/2006 | Othmer | |
| 2008/0004962 A1 | 1/2008 | Muthukrishnan et al. | |
| 2008/0126226 A1 | 5/2008 | Popkiewicz et al. | |

FOREIGN PATENT DOCUMENTS

| | | |
|---|---|---|
| EP | 0 681 181 | 11/1995 |
| GB | 2 324 155 | 10/1998 |
| JP | 06-316394 | 11/1994 |
| JP | 06-317563 | 11/1994 |
| JP | 10-111276 | 4/1998 |
| JP | 2001-074614 | 3/2001 |
| WO | WO 2004/055490 | 7/2004 |

OTHER PUBLICATIONS

English Translation of Office Action dated Jun. 6, 2013 from the Chinese Patent Office for corresponding Application No. 2009-80153115.1.

English Translation of Office Action dated Sep. 11, 2013 from the Japanese Patent Office for corresponding Application No. 2011-544072.

* cited by examiner

DEVICE FOR MONITORING METAL WIRES IN A TIRE

RELATED APPLICATIONS

This is a U.S. national stage under 35 USC §371 of application No. PCT/FR2009/052709, filed on Dec.28, 2009.

This application claims the priority of French application no. 08/59166 filed Dec.31, 2008, the entire content of which is hereby incorporated by reference.

FIELD OF THE INVENTION

The present invention relates to the technical field of tires.

BACKGROUND OF THE INVENTION

A tire comprises several rubber profiled elements superposed on one another and reinforcing threads embedded in the rubber of some of these profiled elements. The term "thread" is to be interpreted here in a general sense. Thus, in what follows, a monofilament thread, a multifilament thread, a cord or a folded yarn for example will be termed a thread. The thread may or may not be surface treated. These threads form plies and are laid substantially parallel to one another within one and the same ply. The threads reinforce the tire to improve its strength and robustness. Some of these threads are made of a magnetic material, for example of steel, notably in tires for vehicles of the heavy vehicle type. The embedded threads form plies.

In order to monitor or check the condition of a tire, notably when the tire is worn, it is recommended that each reinforcing thread be checked in order to make sure than none of them has a defect that could compromise the integrity of the tire. The term "defect" is to be interpreted here as referring to an irregularity in the thread. This irregularity could notably be a cut, a destranding, or alternatively a significant reduction in the cross section of the thread as a result of the wearing, corroding or oxidation of the thread.

The prior art discloses a checking facility that uses X-ray inspection. However, such a facility is relatively expensive and requires a high level of investment.

Also, document U.S. Pat. No. 6,005,388 discloses a device for checking the tire. The device comprises a receiver member that receives a magnetic flux generated from two induction members. The magnetic flux generates, within the receiver member, a condition signal representative of the threads facing the receiver member. However, such a device is capable of roughly identifying a region containing a number of threads which may possibly include defective threads, without being capable of identifying precisely which threads are the defective ones.

SUMMARY OF THE INVENTION

An object of the invention is to make it possible to check for and/or detect any defects there might be in each thread of the tire and to identify which, if any, threads are defective and do so at a relatively low cost. Another object of the invention is to allow the checking of plies the threads of which make different angles with respect to the circumferential direction of the tire.

To this end, one aspect of the invention is directed to a device for checking a tire reinforcing thread, comprising:

at least one induction member that induces a magnetic flux in the thread that is to be checked, a support made of magnetic material supporting the induction member, the support having the overall shape of a U and comprising first and second legs that conduct the magnetic flux into the thread for checking, the ends for conducting the magnetic flux into the thread for checking of the first and second legs defining a direction of alignment of the device, at least one receiver member that receives the magnetic flux flowing through the thread for checking located between the first and second legs, in which device the dimensions of the receiver member are arranged so as to measure only the magnetic flux flowing through the thread for checking when, in operation, the direction of alignment of the device is substantially parallel to the direction in which the thread for checking runs.

In other words, the dimensions of the receiver member are designed so as to measure only the magnetic flux flowing through the thread for checking when, during operation, the alignment of the device is directed parallel to the direction of the said thread.

The device according to the invention makes it possible to detect any defect there might be thread by thread and to pinpoint the defect precisely, unlike the device of the prior art. It is thus possible to count and identify precisely each thread that is exhibiting a defect. Specifically, the overall U shape allows the device according to the invention to be oriented in such a way that the direction of alignment is oriented substantially in the direction of the thread for checking. The magnetic flux generated by the induction member passes only through the thread situated in line with the legs. Thus it is possible to check this one thread alone using the receiver member which, by being situated between the legs, detects any magnetic leakage there might be without the other threads adjacent to the thread that is being checked disrupting the detection.

It will be noted that the smaller the dimension of the receiver member in relation to the diameter of the thread being checked, the better will be the precision with which the defective thread can be pinpointed.

The dimensions of the induction member or members may be greater than the dimensions of the receiver member. The induction members may thus cover or "illuminate" a number of threads, for example 3 to 4 threads, without that preventing thread by thread checking. Specifically, because of the way in which the device is arranged when in operation, the receiver member will detect any potential flux leakage from just the one thread in line with which it is positioned without in any way detecting any potential flux leakages from the other threads with which it is not aligned.

If a branch were to be positioned in line with an adjacent thread that ran in a different direction from that of the thread being checked, the flux flowing through this adjacent thread would not be closed by the other leg, which means that any parasitic flux from this adjacent thread is unable to disrupt the checking of the thread that is intended to be checked.

Thread by thread checking therefore relies on the physical principle of a magnetic flux being induced in each thread by at least one of the legs, and this flux being detected by the receiver member that receives the flux or fluxes.

Further, the more closely spaced the legs, the smaller the area checked. Thus, a defect in each thread can easily be pinpointed by moving the device along each thread. The head of the receiver member has, for example, dimensions that are suitable in relation to the distance or spacing between two consecutive threads that are to be checked. The device therefore detects the presence of any defect in a thread independently of whether or not there is a defect in one of the threads contiguous with the thread being checked.

Furthermore, such a device has the advantage of allowing non-destructive testing of the tire or of the reinforcing ply.

For preference, the receiver member comprises a flux receiver head which, in the direction perpendicular to the direction of alignment, has a dimension substantially smaller than or equal to the diameter of the thread. The width of the receiver head refers to the dimension of the part that forms the sensor of the receiver member. This part is specific to each type of sensor. Because the receiver head has a dimension that is smaller than or equal to the diameter of the thread, the detection signal will therefore be at a maximum when it is placed above the thread being checked, the threads of course not being in contact with one another and being separated by a space.

Advantageously, the dimension of the receiver head is less than or equal to 5 mm, or even 3 mm and preferably 2 mm.

In general, the threads for checking have a diameter smaller than 5 mm and most of them have a diameter varying between 1 to 2 mm, and are spaced apart by a spacing of at least 1 mm. Hence, in practice, the dimension of the receiver head can beneficially range between 2 and 3 mm, so as to allow a wide variety of tires to be checked.

For preference, the detection member is situated equal distances from the first and second legs and this improves the signal/noise ratio.

In one embodiment, the receiver member is conventionally of the inductive type and comprises a receiver coil. It comprises a magnetic sensor of the magneto-resistive sensor type, the magneto-impedance sensor type or the Hall-effect type. Optionally, the receiver member may comprise a magnetic sensor such as an anisotropic magneto-resistive sensor, a giant magneto-resistive sensor or a giant magneto-impedance sensor.

The induction member itself may be of the inductive type powered by an AC or a DC source. Optionally, if the receiver member operates in a static mode, it may be made up of one or more permanent magnets.

The device is able to induce a magnetic field and a corresponding magnetic flux in the or each thread. If there is a defect, the reluctance of the or each checked thread varies and this results in a variation in the induced field and in the magnetic flux.

In another embodiment, the support supports first and second induction members that induce a first and a second magnetic flux in the magnetic support and in the or each thread. The receiver member is situated between the first and second induction members so that the first and second magnetic fluxes are able to generate a signal in the receiver member.

The signal may, for example, and depending on the type of detection member, be an electromotive force, an electrical voltage or a variation in resistance.

The first and second induction members advantageously each create a magnetic flux of similar intensity and of a direction such that the flux is at least partially cancelled at the receiver member.

In the case of an electromotive force and if a defect is present, the device is able to detect a variation in the measured electromotive force with respect to a reference value for the electromotive force.

According to other optional features:
The device is arranged in such a way that each first and second magnetic flux is able to flow respectively in a first and a second part of the thread which part is situated between the receiver member and either the first or the second leg respectively.

Each first and second induction member respectively comprises first and second induction coils, each first and second induction coil being arranged respectively around the first and second legs.

The receiver member comprises a core around which is arranged a receiver coil that receives the first and second electromagnetic fluxes, the core forming the receiver head that receives the first and second magnetic fluxes.

Another aspect of the invention is directed to a method of monitoring or checking a tire or a ply comprising reinforcing threads which are made of a magnetic material and laid substantially parallel to one another at a given angle to the circumferential direction of the tire or to the longitudinal direction of the ply, using a checking device as defined hereinabove, wherein each thread of the tire or of the ply is checked in succession independently of one another.

The method according to the invention makes it possible to check the condition of each thread independently of the condition of the threads contiguous with the thread being checked. Thus, it is possible to identify precisely which thread it is that is exhibiting a defect.

The method can be applied to an unvulcanized green tire, to a new vulcanized tire, to a retreaded tire or else to a ply of rubber.

Advantageously, the receiver member is kept in contact with the tire or with the ply being checked.

Likewise it proves advantageous to keep the or each induction member in contact with the tire or with the ply being checked.

For preference, the receiver member comprises a flux receiver head which, in the direction perpendicular to the direction of alignment, has a dimension substantially smaller than or equal to the diameter of the thread.

According to an optional feature, the tire or the ply is moved with respect to the device and a signal representative of the condition of the or each thread as a function of the relative movement of the tire or of the ply with respect to the device is measured.

In one embodiment, the value of the measured signal is compared against a reference value so that any defect with the or each thread can be detected.

In another embodiment, a geometric characteristic of the or each thread is determined as a function of a variation in the measured signal.

In an alternative form:
the tire or the ply is moved circumferentially in a longitudinal direction with respect to the device over a given circumferential length or a given length, respectively,
the variation in the signal as a function of the movement of the tire or of the ply is measured,
the following are determined:
a number of threads in the circumferential length of the tire or the length of the ply, and/or
a spacing between each thread in the circumferential length of the tire or the length of the ply.

In general, the tire comprises threads that are uniformly spaced. The signal therefore varies periodically. According to how the device is set up, the presence of a thread corresponds for example to a minimum or to a maximum of the signal. From this then it is possible to deduce the number of threads in the circumferential length of tire or the length of ply and, by knowing the speed of relative movement between the tire or the ply and the device, the spacing between each thread in the circumferential length of tire or the length of ply.

In another alternative form:
the device is rotated about an axis substantially perpendicular to a surface, called the circumferential surface, of the tire or a surface, called the longitudinal surface, of the ply,
the variation in the signal as a function of the angle of rotation of the device is measured,
the angle formed by each thread with the circumferential direction of the tire or with the longitudinal direction of the ply is determined.

Depending on the way in which the device is set up, the presence of a thread corresponds, for example, to a minimum or to a maximum of the signal when the device is oriented substantially parallel to the thread, that is to say when the direction of alignment is substantially parallel to the thread being checked. Thus, when the device is rotated, the signal varies until it reaches a turning point, for example a maximum, when the angle of rotation of the device is substantially equal to the angle formed by the thread with the longitudinal direction of the ply or with the circumferential direction of the tire.

BRIEF DESCRIPTION OF THE DRAWINGS

The invention will be better understood from reading the following description, given solely by way of non limiting example and made with reference to the drawings in which.

DETAILED DESCRIPTION OF THE DRAWINGS

Figure 1:
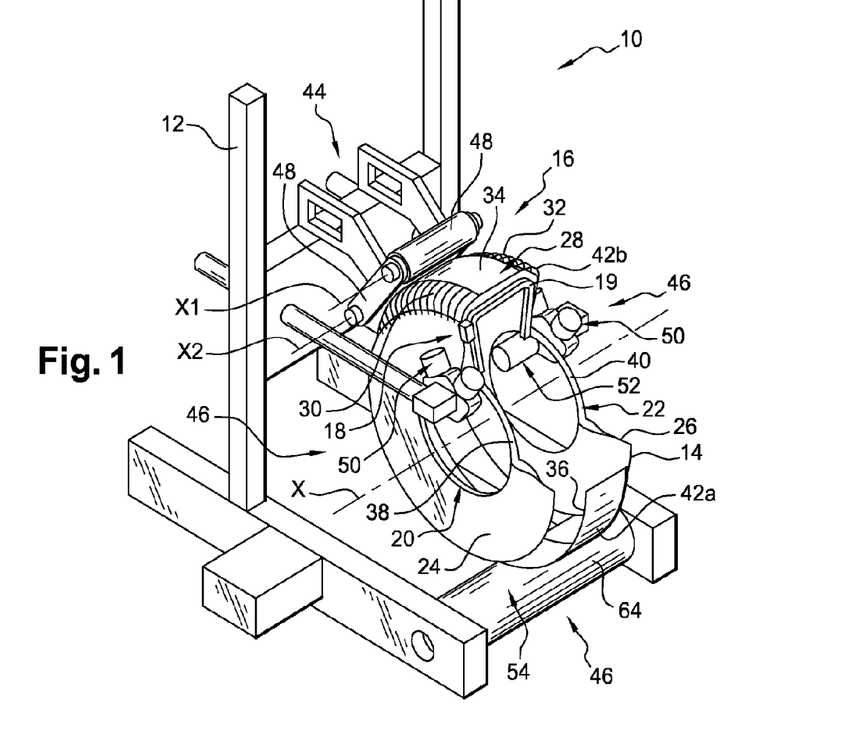
FIG. 1 is a perspective view of a checking facility comprising a checking device according to a first embodiment able to implement a checking method according to a first embodiment.
Figure 2:
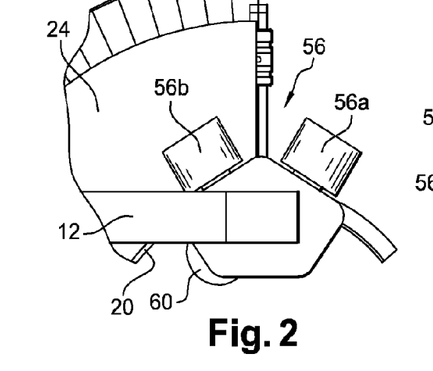
FIG. 2 is a side view of part of the facility of FIG. 1.
Figure 3:
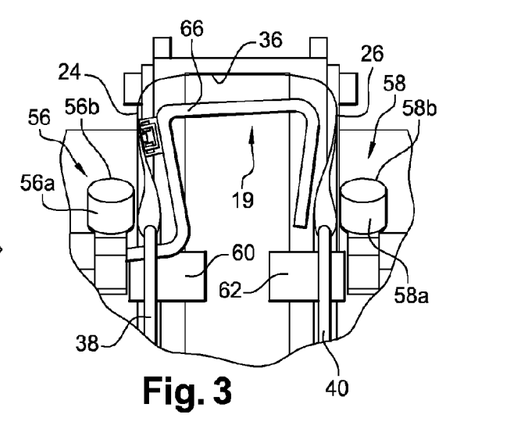
FIG. 3 is a view of the facility of FIG. 1 in cross section.

FIGS. 1 to 3 depict a facility comprising a checking device according to a first embodiment and denoted by the general reference 10.

The facility 10 comprises a tire 14 support frame 12. As an alternative, the frame 12 could support an unvulcanized green tire 14. The facility 10 also comprises means 16 of rotating the tire 14. The facility 10 comprises a device 18 for checking the tire 14 and means 19 for guiding the device 18.

The tire 14 exhibits substantial symmetry of revolution about an axis of revolution X. The tire 14 comprises first and second radially internal catching edges 20, 22 that delimit it. The tire 14 comprises first and second sidewalls 24, 26 and a tread 28. The tread 28 is axially delimited by first and second ends 30, 32 known as shoulders.

The tire 14 additionally comprises a radially external, called circumferential, tread surface 34 and a radially internal surface 36. The tire 14 also comprises first and second circular bead wires 38, 40 substantially coaxial with the axis X. Finally, the tire 14 comprises reinforcing threads 42a, 42b made of a magnetic material, in this instance a metallic material, here made of steel. The reinforcing threads 42a situated under the tread 28 form the crown reinforcing belt. The reinforcing threads 42b running between the first and second bead wires 38, 40 form the carcass reinforcing ply. The wires 42a, 42b are grouped together in various plies and laid substantially parallel to one another within one and the same ply.

The means 16 of rotation comprise drive means 44 for driving the tire 14 and guide means 46 for guiding it. The means 44 comprise two motorized rollers 48 that rotate about axes X1, X2 substantially parallel to the axis X and that are positioned in contact with the tread 28 so as to rotate the tire 14. The means 42 also comprise guide means 50, 52, 54 for the axial, radial and circumferential guidance of the tire 14. The axial guidance means 50 comprise first and second pairs 56, 58 of guide rollers 56a, 56b and 58a, 58b. The first and second pairs 56, 58 are positioned substantially symmetrically with respect to an axial median plane of the tire 14. The guide rollers 56a-b, 58a-b are respectively positioned in contact with the first and second sidewalls 24, 26. The radial guidance means 52 comprise first and second guide rollers 60, 62 positioned respectively in contact with the first and second edges 20, 22. The circumferential guidance means 54 comprise a roller 64 for rolling the tire 14 free to rotate about an axis X3 substantially parallel to the axis X.

The guide means 19 of the device 18 are arranged so that the device 18 follows the contour of the radially internal surface 36 when the device 18 is moved along the guide means 19. The guide means 19 comprise a guide forming a rail 66. The guide 66 is in the overall shape of an inverted U.

Figure 4:
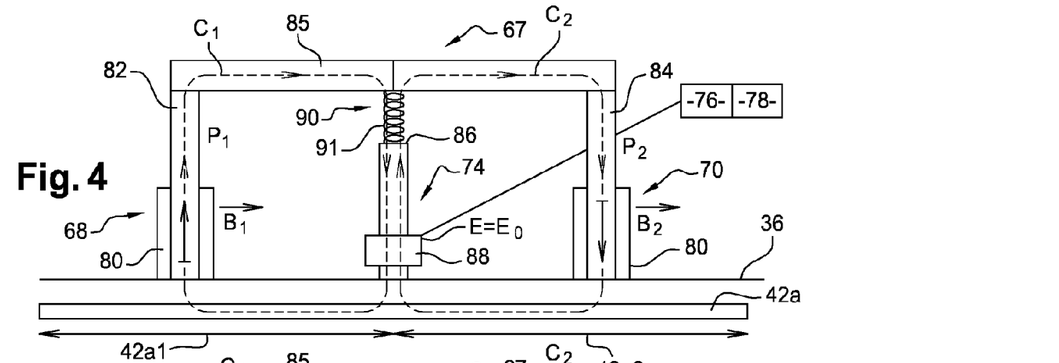
FIGS. 4 and 5 are diagrams illustrating a device of the facility of FIG. 1.
Figure 5:
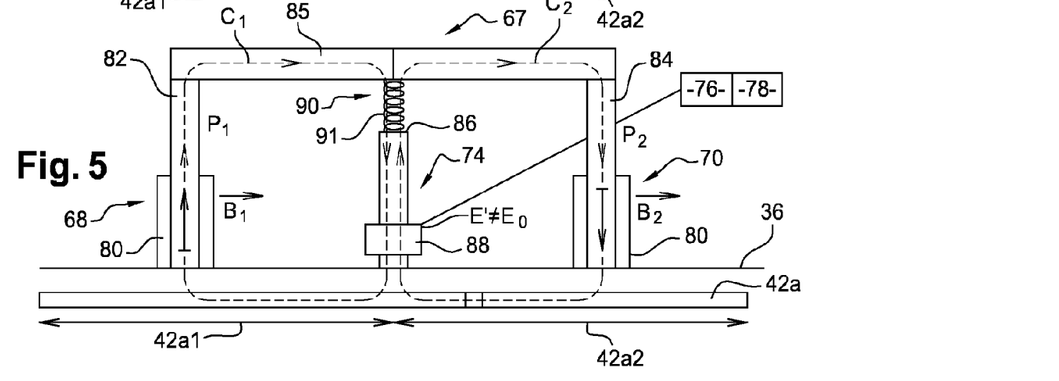

With reference to FIGS. 4 and 5, the device 18 is of the eddy current type. The device 18 comprises a support 67 made of magnetic material supporting first and second induction members 68, 70 that respectively induce first and second electromagnetic fields B1, B2 respectively generating first and second magnetic fluxes P1, P2 in the support 67 and each thread 42a, 42b. Further, the device 18 comprises a receiver member 74 that receives the first and second fluxes P1, P2. The receiver member 74 is situated between the first and second induction members 68, 70 so that the first and second fields B1, B2 are capable of generating a signal representative of the condition of each thread 42a, 42b in the member 74. The fields B1, B2 generate a signal in the receiver member 74, and the nature of this signal is dependent on the type of receiver as was already explained earlier. For the sake of convenience in the following, it will be considered that the representative signal in question is an electromotive force denoted E.

The receiver member 74 is situated equal distances from the members 68, 70 and therefore from the legs 82, 84. The device 18 is set up in such a way that the algebraic values of the fields B1 and B2 are such that the value of the signal (the electromotive force E) is at a minimum, or even zero, if the thread exhibits symmetry, and exhibits no defect. It is then possible to alter the amplitude and phase of the fields B1 and B2 in an attempt to cause the value of the signal (the electromotive force E) to tend toward a value for which the signal has a minimum amplitude.

As an alternative, the member 74 may be closer to one of the members 68, 70 than to the other. The device 18 also comprises means 76 for measuring the signal (the electromotive force E) and means 78 for comparing the signal (the electromotive force E) against a reference value (electromotive force $E_0$).

Each induction member 68, 70 comprises an induction coil 80. The support 67 has the overall shape of a U comprising first and second magnetic legs 82, 84 that respectively conduct the first and second fluxes P1, P2 into each thread 42a, 42b. The support also comprises a crossbar 85 connecting the legs 82, 84 together. Each induction coil 80 is arranged around each leg 82, 84.

Each first and second leg has an end for conducting each magnetic flux P1, P2 into the thread being checked. The ends define a direction of alignment. The first and second induction members 68, 70 and the receiver member 74 are also substantially aligned in the direction of alignment. The direction of alignment is substantially parallel to the direction in which each thread to be checked runs. Thus, the device is arranged in such a way as to measure only the magnetic flux flowing through the thread to be checked when, in operation, the direction of alignment is directed substantially parallel to the direction in which the thread being checked runs.

The receiver member 74 comprises a receiver head 86, in this instance a core around which a coil 88 for receiving the fluxes P1, P2 is arranged. The legs 82, 84, the crossbar 85 and the core 86 are made of ferrite. The head 86 is intended to be positioned in line with the surface 34 of the tire 14 and has relevant dimensions for receiving the magnetic fluxes P1, P2 such that the receiver member is capable of detecting a variation in flux when the device is moved with respect to the tire 14 over a distance equal to the spacing separating two contiguous threads 42a, 42b for checking. The head 86 has a substantially cylindrical shape with a diameter substantially equal to 1 mm and a length of approximately 33 mm. The coil 88 comprises several turns of a wire wound around the core 86. The wire has a diameter less than 1 mm and in this particular instance of 0.6 mm. The coil 88 comprises one hundred or so turns, specifically 103 turns distributed over four superposed layers. The coil 88 extends over a height of 2 mm over the core 86. In the example depicted, the resonant frequency of the receiver member 74 is 960 kHz. Further, the member 74 has an impedance of 73 Ω at 100 kHz for an inductance of 115 µH. A coil of this type is capable of detecting a variation in flux as the said device passes across the spacing separating two contiguous threads for checking.

The device also comprises means 90 for keeping the core 86 in contact with the surface 36. These means 90 notably comprise a spring 91.

With reference to FIGS. 4 and 5, the thread 42a comprises first and second parts 42a1, 42a2. The first part 42a1 is situated between the member 74 and the induction member 68. The second part 42a2 is situated between the member 74 and the induction member 70. The device 18 is arranged in such a way that each first and second magnetic flux P1, P2 is capable of flowing respectively through the first and through the second part 42a1, 42a2 of the thread 42a.

If there is no defect in the thread 42 (FIG. 4) then the two magnetic fluxes P1, P2 then passing through the receiver member 74 generate a signal (an electromotive force $E_0$), called the reference signal, that corresponds to two closed magnetic circuits C1, C2 depicted in dotted line. If the induction members 68, 70 are strictly identical, the value of the reference signal (the electromotive force $E_0$) is equal to 0 when the phase of the voltages creating the fluxes P1 and P2 is correctly adjusted. As an alternative, the members 68, 70 have different characteristics so that the value of the reference signal (the electromotive force $E_0$) is different from 0.

If there is a defect in the thread 42 (FIG. 5), which in this instance there is in the second part 42a2, the two magnetic fluxes P1, P2 then pass through the receiver member 74, generating an electromotive force E' which, in the example depicted, corresponds to a closed magnetic circuit C1 and to a magnetic circuit C2 that exhibits higher reluctance than the magnetic circuit C2 in FIG. 4. The value of the measured signal (the electromotive force E') is different from the value of the reference signal (electromotive force $E_0$).

The facility 10 is capable of implementing a checking method according to a first embodiment, of which the key stages associated with the invention will be described hereinafter.

The tire 14 is positioned in the facility 10. The first and second catching edges 20, 22 are positioned respectively on the first and second guide rollers 60, 62 and the first and second sidewalls 24, 26 are positioned respectively against the guide rollers 56a-b, 58a-b.

The rollers 48 are then pressed firmly against the tread surface 34.

The tire 14 is then checked with a view to detecting any potential defects with the threads 42a, 42b of the tire 14. Each thread 42a, 42b is checked in succession independently of one another.

To do that, the first and second induction members 68, 70 are positioned facing the tire 14 and the core 86 is kept in contact with the radially internal surface 36. The induction members 68, 70 can also be kept in contact with the said internal surface 36.

The tire 14 is then made to rotate about the axis X using the rollers 48 and the value of the signal (electromotive force E) generated in the receiver member 74 as a function of the relative movement of the tire 14 with respect to the device 18 is measured. The core 86 is kept in contact with the internal surface 36. The tire 14 is made to effect one revolution. Alternatively, and to make the detection of any potential defect more reliable, the tire 14 is made to effect a number of revolutions. During this measurement, each value of the signal (of the electromotive force E) measured for each thread is compared against the value of the reference signal (the electromotive force $E_0$), so that any defect there may be in each thread 42a, 42b can be detected.

A first portion of the tire 14 facing the first and second induction members 68, 70 is checked in this way. This portion forms a circular band the width of which is substantially equal to the distance between the first and second induction members 68, 70.

The device 18 is then moved axially and/or radially along the contour of the surface 36 and the tire 14 is rotated again about the axis X. A second circular band adjacent to the first portion is checked in this way.

For each portion and when a defect is detected, a position of the tire 14 about the axis X with respect to a reference position is measured. In this particular instance, the angular position of the tire 14 with respect to a reference angular position is determined. In the embodiment illustrated, the position of the device 18 in the guide means 19 when a defect is detected is also recorded so as to determine which circular band contains the defect. By performing successive iterations, the entire tire 14 is checked.

Figure 6:
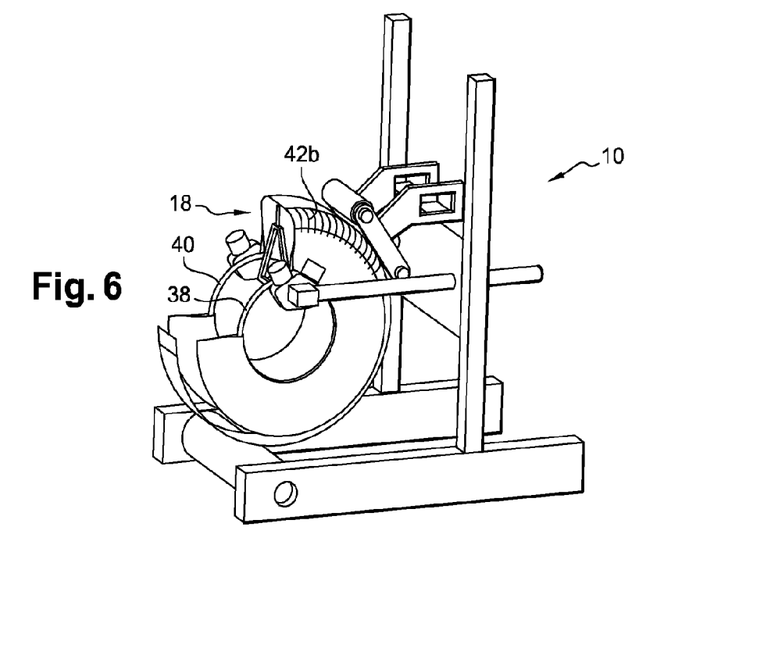
FIG. 6 is a view similar to FIG. 1 of a facility comprising a device according to a second embodiment capable of implementing a checking method according to a second embodiment.
Figure 7:
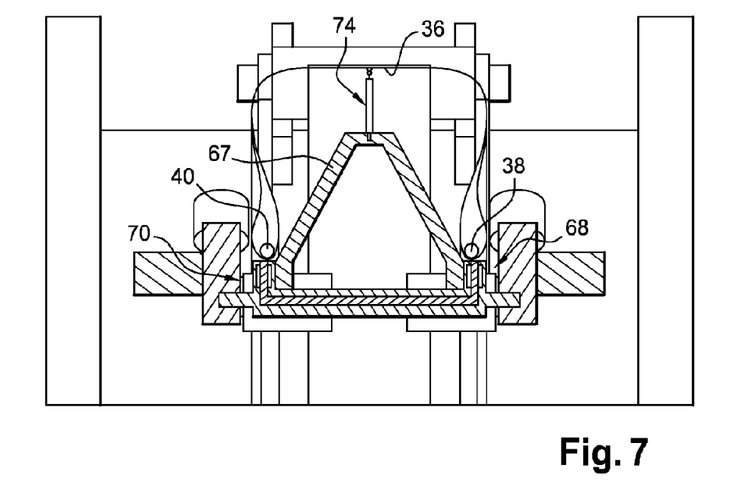
FIG. 7 is a view similar to FIG. 3 of the facility of FIG. 6.

FIGS. 6 and 7 illustrate a facility according to a second embodiment. Elements similar to those depicted in the preceding figures are denoted by the same references.

Unlike in the first embodiment, the facility 10 does not comprise guide means 19 for guiding the device 18. The first and second induction members 68, 70 and the receiver member 74 are axially and radially fixed with respect to the tire 14.

In this embodiment, the member 74 is positioned substantially in an axial median plane of the tire 14 and the head 86 is positioned in contact with the internal surface 36.

The installation 10 in FIGS. 6 and 7 is capable of implementing a checking method according to a second embodiment.

In this embodiment, each first and second induction member 68, 70 is positioned axially substantially facing each first and second bead wire 38, 40 respectively. The core 86 is kept in contact with the internal surface 36 so that any defect with each thread 42b running between the first and second bead wires 38, 40 can be detected.

Figures 8, 9:
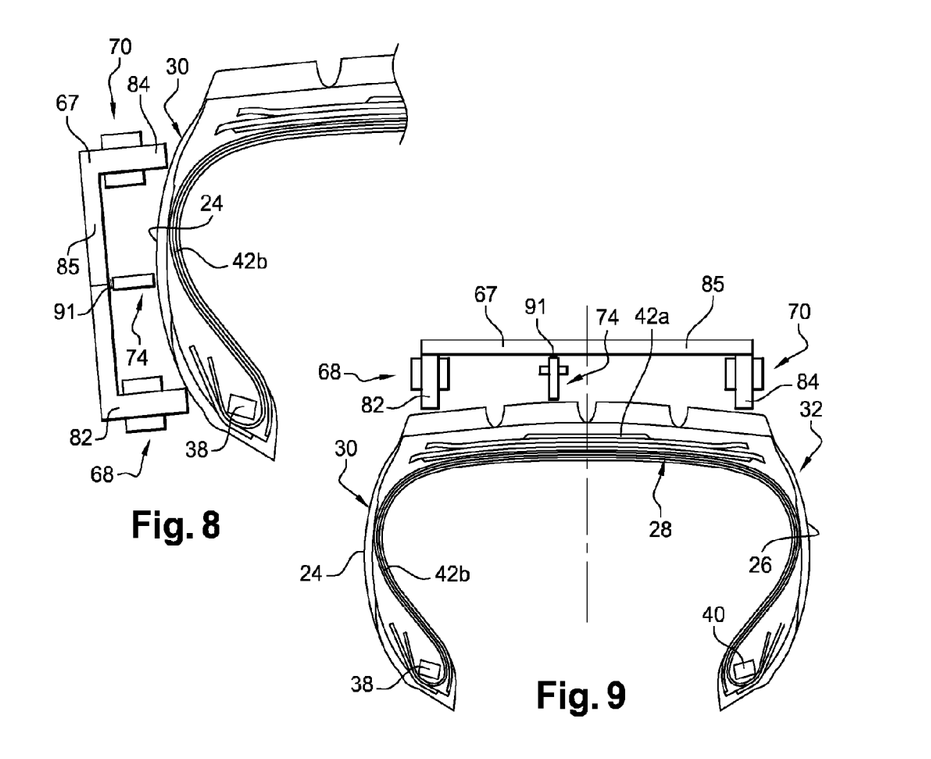
FIGS. 8 and 9 schematically and respectively illustrate facilities comprising devices according to third and fourth embodiments capable of implementing checking methods according to third and fourth embodiments.

FIGS. 8 and 9 depict a facility according to third and fourth embodiments. Elements similar to those depicted in the preceding figures are denoted by the same references.

The facility 10 in FIG. 8 is capable of implementing a checking method according to a third embodiment.

In this embodiment, the first induction member is positioned axially facing the end 30, 32 and the second induction member is positioned axially facing the bead wire 38, 40. The head 86 is kept in contact with the sidewall 24, 26 and the tire 14 is rotated and each sidewall 24, 26 is thus respectively checked so that any defect with each thread 42b in the carcass reinforcing ply situated in a region called the sidewall, running between the end 30, 32 and the bead wire 38, 40, can be detected.

The facility 10 of FIG. 9 is capable of implementing a checking method according to a fourth embodiment.

In this embodiment, each first and second induction member is positioned axially substantially facing each first and second axial end 30, 32 of the tread 28 respectively. The head 86 is kept in contact with the external surface 34 of the tread 28 and the tire 14 is rotated so that any defect in each thread 42b of one of the carcass reinforcing plies can be detected.

Figure 10:
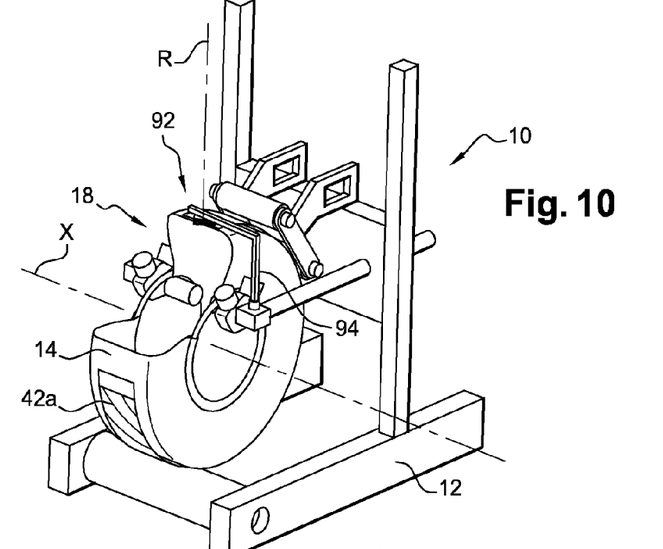
FIG. 10 is a perspective view of a facility according to a fifth embodiment capable of implementing a checking method according to a fifth embodiment.
Figures 11, 12:
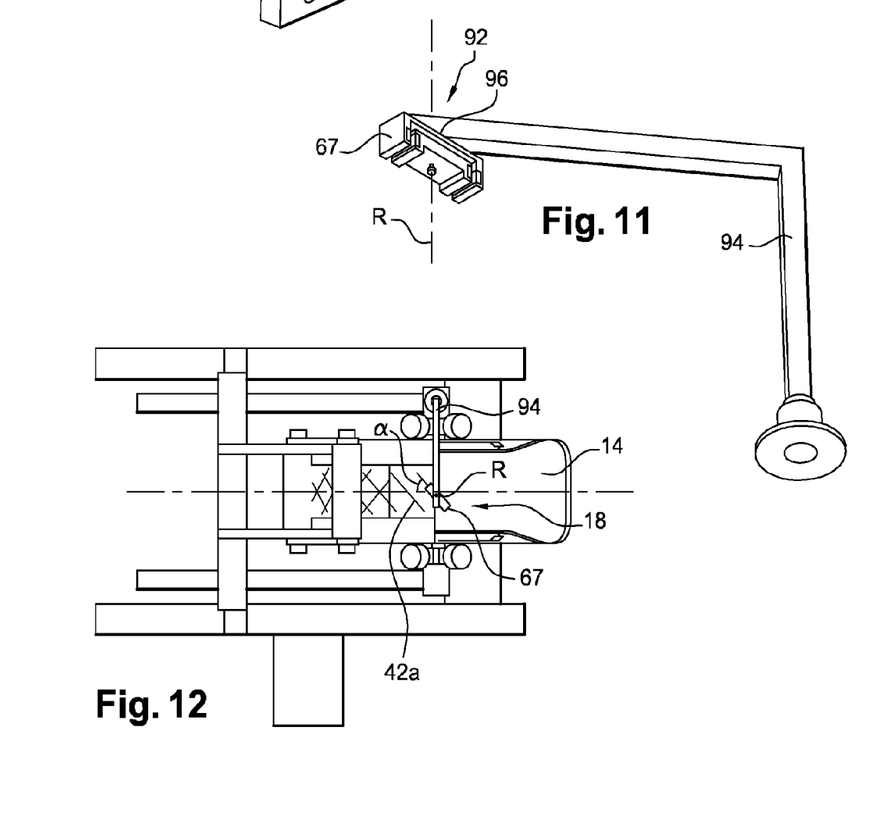
FIG. 11 illustrates means of articulation of the checking device of the facility of FIG. 10.
FIG. 12 is a view of the facility of FIG. 10 from above.

FIGS. 10 to 12 depict a facility according to a fifth embodiment. Elements similar to those depicted in the previous figures are denoted by the same references.

The facility 10 also comprises means 92 of articulating the device 18 with respect to the tire 14. The articulation means 92 form means of articulating in terms of rotation the support 67 about a radial axis R substantially perpendicular to the axis of rotation X of the tire and normal to the circumferential surface 34. The articulation means 92 comprise an arm 94 to which the device 18 is attached by means of a rotary joint 96.

The facility 10 of FIGS. 10 to 12 is capable of implementing a checking method according to a fifth embodiment.

Unlike in the previous embodiments in which the threads 42b of the carcass reinforcing ply extending in a substantially radial direction are checked, in the fifth embodiment, it is the threads 42a of the crown reinforcing plies that are checked.

The threads 42a run in a direction that makes an angle smaller than 90° with respect to the circumferential direction of the tire 14. In the particular instance illustrated in FIGS. 10 to 12, this direction forms an angle ±α of ±45° with the circumferential direction of the tire 14.

The device 18 is pivoted about the axis R by an angle ±α, here ±45°, and the tire 14 is checked in a similar way to the way described in the first embodiment.

Figures 13, 14:
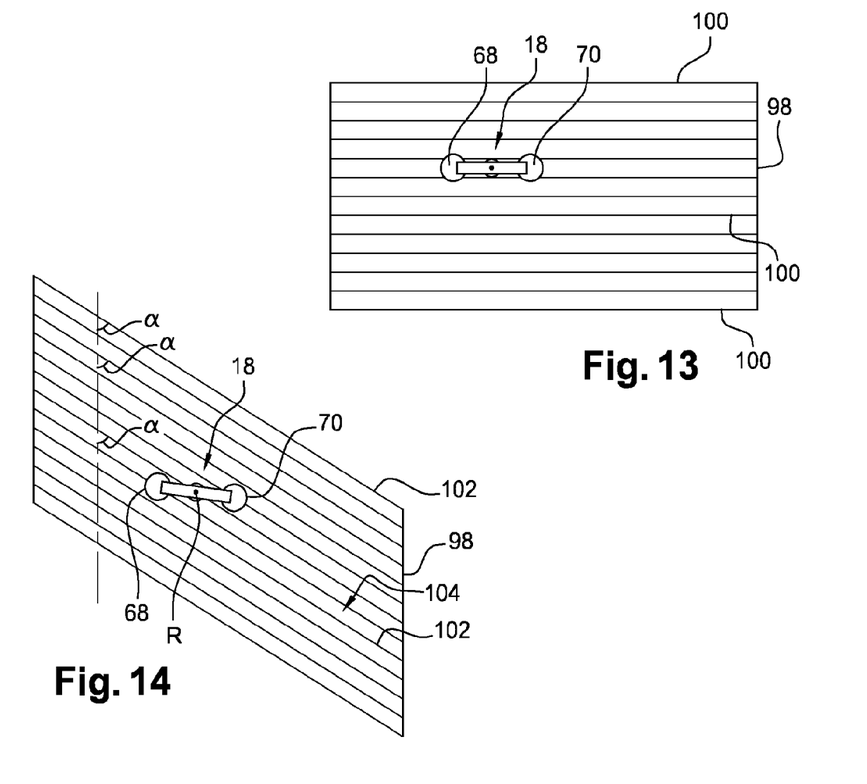
FIGS. 13 and 14 illustrate checking methods according to sixth and seventh embodiments.

FIG. 13 schematically depicts a device according to a sixth embodiment. Elements similar to those depicted in the preceding figures are denoted by the same references.

The device 18 according to the sixth embodiment can be used to check a reinforcing ply 98. The ply 98 comprises metal threads 100 coated in a rubber compound, running substantially parallel to one another and making a given angle to the longitudinal direction of the ply 98. Unlike the facility according to the fifth embodiment, the facility 10 according to the sixth embodiment does not comprise any means 16 for rotating the tire 14 but comprises means (not depicted) for moving the reinforcing ply 98. The threads 100 are arranged substantially perpendicular to the longitudinal direction of the reinforcing ply 98 in the case of a carcass reinforcing ply like the one illustrated in FIG. 13.

The facility 10 of FIG. 13 is capable of implementing a checking method according to a sixth embodiment.

The reinforcing ply 98 is moved with respect to the device 18. The reinforcing ply 98 is moved translationally in a direction substantially parallel to the longitudinal direction of the reinforcing ply 98 over a given length L. A variation in the value of the signal (of the electromotive force) as a function of the movement of the reinforcing ply 98 is measured. Then, because the speed at which the reinforcing ply 98 is moving is known, a geometric characteristic of the threads 100 is determined as a function of the variation in the value of the measured signal (electromotive force). In this particular instance, it is a number of threads 100 in the length of the reinforcing ply 98 moved that is determined. As an alternative, it is a spacing between the threads 100 in the moved length of reinforcing ply 98 that is determined.

As an alternative, a tire 14 is checked. In this alternative, circumferential revolution about the axis X is induced with respect to the device 18 respectively over a given circumferential length and the variation in signal as a function of the movement of the tire 14 is measured. In this way, the number of threads in the circumferential length of the tire 14 and/or the spacing between the threads 100 in the circumferential length of the tire 14 is or are determined.

FIG. 14 depicts a device according to a seventh embodiment. Elements similar to those depicted in the preceding figures are denoted by the same references.

Unlike the reinforcing ply 98 in the sixth embodiment, the reinforcing ply 98 comprises threads 102 running in a direction that makes an angle ±α smaller than 90° with the longitudinal direction of the ply, as in the case of a crown reinforcing ply as illustrated in FIG. 14. Here, the angle α is approximately equal to ±45°.

In a similar way to the facility according to the fifth embodiment, the facility 10 according to the seventh embodiment comprises means (not depicted) of rotational articulation of the device 18 with respect to the reinforcing ply 98 about an axis R substantially perpendicular to the longitudinal surface 104 of the reinforcing ply 98 and passing through the head 86.

The facility 10 in FIG. 14 is also capable of implementing a checking method according to a seventh embodiment.

The orientation of each thread 102 is checked in succession independently of one another. The device 18 is rotationally moved about the axis R. The variation in the value of the signal (the electromotive force) as a function of an angle of rotation of the device 18 about the axis R is measured. Next, the angle formed by each thread 100 with the longitudinal direction of the ply 98 is determined.

As an alternative, a tire 14 is checked. In this alternative, the device is moved rotationally about the axis R substantially perpendicular to the surface 34 of the tire 14 and the variation in signal as a function of the angle of rotation of the device is measured. Next the angle formed by each thread 102 with the circumferential direction of the tire 14 is determined.

Figure 15:
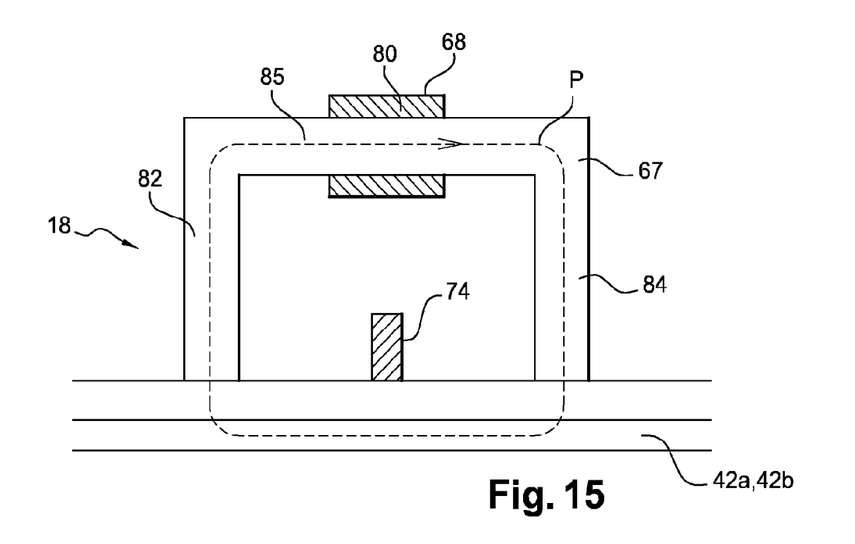
FIG. 15 illustrates a device according to an eight embodiment.

FIG. 15 depicts a device according to an eighth embodiment. Elements similar to those depicted in the preceding figures are denoted by the same references.

The device 18 comprises an induction member 68 that induces a magnetic flux P in each thread 42a, 42b. The device 18 also comprises a receiver member 74 that receives the magnetic flux P. The device 18 also comprises a support 67 made of a magnetic material and supporting the induction member 68. The support 67 is in the overall shape of a U and has first and second legs 82, 84 for conducting the magnetic flux P into each thread 42a, 42b. The receiving member 74 is situated between the legs 82, 84 and comprises a magnetic sensor, in this instance a magneto-resistive sensor. By way of example, successful use has been made of a magneto-resistive sensor reference AAH004 by NVE, encapsulated in a housing of the MSOP8 type, supplied by that same company.

As an alternative, the member 74 comprises a Hall-effect sensor, a magneto-impedance sensor or any other sensor capable of detecting a magnetic field.

The invention claimed is:

1. A device for checking a tire reinforcing thread made of a magnetic material and having a determined diameter comprising:
    at least one induction member that induces a magnetic flux in the thread that is to be checked;
    a support made of magnetic material supporting the induction member, the support having the overall shape of a U and comprising first and second legs that conduct the magnetic flux into the thread for checking, the ends for conducting the magnetic flux into the thread for checking of the first and second legs defining a direction of alignment of the device; and
    at least one receiver member that receives the magnetic flux flowing through the thread for checking between the first and second legs;
    wherein the dimensions of the receiver member are arranged so as to measure only the magnetic flux flowing through the thread for checking when, in operation, the direction of alignment of the device is substantially parallel to the direction in which the thread for checking runs, and
    wherein the receiver member comprises a core around which is arranged a receiver coil that receives the magnetic flux flowing through the thread for checking, and is movable and comprises means for keeping the core in contact with a radially internal surface of the tire.

2. The device according to claim 1, wherein the receiver member comprises a flux receiver head which, in the direction perpendicular to the direction of alignment, has a dimension smaller than or equal to the diameter of the thread.

3. The device according to claim 2, wherein the dimension of the receiver head in the direction perpendicular to the direction of alignment is less than or equal to 5 mm.

4. The device according to claim 1, wherein the receiver member is situated equal distances from the first and second legs.

5. The device according to claim 1, wherein the receiver member comprises a magnetic sensor of the magneto-resistive sensor type, the magneto-impedance sensor type or the Hall-effect type.

6. The device according to claim 1, wherein the support supports first and second induction members that induce a first and a second magnetic flux in the magnetic support and in the thread.

7. The device according to claim 6, wherein each first and second induction member respectively comprises first and second induction coils each first and second induction coil being arranged respectively around the first and second legs.

8. The device according to claim 6, wherein the receiver member comprises a core around which is arranged a receiver coil that receives the first and second electromagnetic fluxes, the core forming the receiver head that receives the first and second magnetic fluxes.

9. The device according to claim 1, wherein the core extends towards a central part of the support having the overall shape of a U.

10. The device according to claim 1, wherein the means for keeping the core in contact with a radially internal surface of the tire comprises a spring.

11. A method of monitoring or checking a tire or a ply comprising reinforcing threads which are made of a magnetic material and laid parallel to one another at a given angle to the circumferential direction of the tire or to the longitudinal direction of the ply, using a checking device comprising:
    at least one induction member that induces a magnetic flux in the thread that is to be checked;
    a support made of magnetic material supporting the induction member, the support having the overall shape of a U and comprising first and second legs that conduct the magnetic flux into the thread for checking, the ends for conducting the magnetic flux into the thread for checking of the first and second legs defining a direction of alignment of the device; and
    at least one receiver member that receives the magnetic flux flowing through the thread for checking between the first and second legs;
    wherein the dimensions of the receiver member are arranged so as to measure only the magnetic flux flowing through the thread for checking when, in operation, the direction of alignment of the device is substantially parallel to the direction in which the thread for checking runs, and
    wherein the receiver member comprises a core around which is arranged a receiver coil that receives the magnetic flux flowing through the thread for checking, and is movable and comprises means for keeping the core in contact with a radially internal surface of the tire; and
    wherein each thread of the tire or of the ply is checked in succession independently of one another.

12. The method according to claim 11, wherein the receiver member comprises a flux receiver head which, in the direction perpendicular to the direction of alignment, has a dimension smaller than or equal to the diameter of the thread.

13. The method according to claim 11, wherein the tire or the ply is moved with respect to the device and a signal representative of the condition of the or each thread as a function of the relative movement of the tire or of the ply with respect to the device is measured.

14. The method according to claim 13, wherein the value of the measured signal is compared against a reference value so that any defect with the or each thread can be detected.

15. The method according to claim 14, wherein a geometric characteristic of the or each thread is determined as a function of a variation in the measured signal.

16. The method according to claim 15, wherein:
    the tire or the ply is moved circumferentially in a longitudinal direction with respect to the device over a given circumferential length or a given length, respectively,
    the variation in the signal as a function of the movement of the tire or of the ply is measured,
    the following are determined:
        a number of threads in the circumferential length of the tire or the length of the ply, and/or
        a spacing between each thread in the circumferential length of the tire or the length of the ply.

17. A method of monitoring or checking a tire or a ply comprising reinforcing threads which are made of a magnetic material and laid parallel to one another at a given angle to the circumferential direction of the tire or to the longitudinal direction of the ply, using a checking device comprising:

at least one induction member that induces a magnetic flux in the thread that is to be checked;

a support made of magnetic material supporting the induction member, the support having the overall shape of a U and comprising first and second legs that conduct the magnetic flux into the thread for checking, the ends for conducting the magnetic flux into the thread for checking of the first and second legs defining a direction of alignment of the device;

at least one receiver member that receives the magnetic flux flowing through the thread for checking between the first and second legs;

wherein the dimensions of the receiver member are arranged so as to measure only the magnetic flux flowing through the thread for checking when, in operation, the direction of alignment of the device is substantially parallel to the direction in which the thread being checked runs, the method comprising:

moving the tire or the ply with respect to the checking device;

measuring a signal representative of the condition of the or each thread as a function of the relative movement of the tire or of the ply with respect to the checking device;

comparing the value of the measured signal against a reference value so that any defect with the or each thread can be detected;

determining a geometric characteristic of the or each thread as a function of a variation in the measured signal;

rotating the checking device about an axis substantially perpendicular to a surface, called the circumferential surface, of the tire or a surface, called the longitudinal surface, of the ply;

measuring the variation in the signal as a function of the angle of rotation of the checking device;

determining the angle formed by each thread with the circumferential direction of the tire or with the longitudinal direction of the ply; and checking each thread of the tire or of the ply in succession independently of one another.

* * * * *